(12) United States Patent
Oku et al.

(10) Patent No.: US 6,410,806 B2
(45) Date of Patent: Jun. 25, 2002

(54) REDUCTION-TREATED COPPER-BASED CATALYST AND PROCESS FOR PRODUCING α-PHENYLETHYL ALCOHOL USING THE SAME

(75) Inventors: Noriaki Oku, Ichihara; Masaru Ishino, Sodegaura, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/761,830

(22) Filed: Jan. 18, 2001

(30) Foreign Application Priority Data

Jan. 19, 2000 (JP) ........................................ 2000-009841

(51) Int. Cl.⁷ ............................................... C07C 27/00
(52) U.S. Cl. ........................................ 568/814; 502/345
(58) Field of Search ........................... 568/814; 502/345

(56) References Cited

U.S. PATENT DOCUMENTS

| 3,927,120 A | * | 12/1975 | Grane |
| 4,160,746 A | | 7/1979 | Rashkin |
| 5,554,574 A | * | 9/1996 | Tsukada |
| 5,658,843 A | * | 8/1997 | Tsukada |
| 6,046,369 A | | 3/2000 | Oku et al. |

FOREIGN PATENT DOCUMENTS

NL       1009602       3/1999

* cited by examiner

Primary Examiner—Michael L. Shippen
(74) Attorney, Agent, or Firm—Birch, Stewart, Kolasch & Birch, LLP

(57) ABSTRACT

A reduction-treated copper-based catalyst obtained by reducing a copper-based catalyst with hydrogen in the presence of a liquid phase and a process for producing α-phenylethyl alcohol, which comprises hydrogenating acetophenone in the presence of the same.

4 Claims, No Drawings

REDUCTION-TREATED COPPER-BASED CATALYST AND PROCESS FOR PRODUCING α-PHENYLETHYL ALCOHOL USING THE SAME

BACKGROUND OF THE INVENTION

1. Field of the Invention

The present invention relates to a reduction-treated copper-based catalyst and a process for producing α-phenylethyl alcohol using the same. More particularly, the present invention relates to a reduction-treated copper-based catalyst and a process for producing α-phenylethyl alcohol by hydrogenating acetophenone in the presence of a copper-based catalyst, which can keep the lowering of catalyst activity at an extremely low level. In addition, α-phenylethyl alcohol is useful, for example, as a raw material for production of styrene, and a raw material for production of various perfumes.

2. Description of Related Arts

A copper-based catalyst is known as a hydrogenation catalyst. And, it is known that α-phenylethyl alcohol can be produced by hydrogenating acetophenone with the copper-based catalyst. For example, a process of hydrogenating acetophenone using a copper-chromite catalyst which contains barium, zinc and magnesium is disclosed in JP-A-59-27216.

By the way, when the reaction is carried out by flowing a fluid for reaction into a reactor in which the copper-based catalyst is packed, it is required that copper oxide in the catalyst is reduced to copper as an activation treatment of the catalyst, but there have been problems that the catalyst activity is lowered remarkably depending on reduction process, the catalyst cannot sufficiently exhibit the quality over long period, and it is disadvantageous from the industrial view point in particular.

SUMMARY OF THE INVENTION

Under these circumstances, an object of the present invention is to provide a reduction-treated copper-based catalyst and a process for producing α-phenylethyl alcohol by hydrogenating acetophenone in the presence of the copper-based catalyst, which can keep the lowering of catalyst activity at an extremely low level.

Namely, the present invention relates to a reduction-treated copper-based catalyst obtained by reducing a copper-based catalyst with hydrogen in the presence of a liquid phase, and a process for producing α-phenylethyl alcohol, which comprises hydrogenating acetophenone with said reduction-treated copper-based catalyst.

DETAILED DESCRIPTION OF THE INVENTION

The copper-based catalyst used in the present invention means a catalyst containing CuO as a main component. The content of CuO in the catalyst is usually 10 to 90% by weight and preferably 20 to 80% by weight. The too low and too high amounts of the content happen to cause the lowering of hydrogenation activity. The components other than CuO in the catalyst include various metal oxides such as $Cr_2O_3$, ZnO, $Fe_2O_3$, $Al_2O_3$, $La_2O_3$, $Sm_2O_3$, $CeO_2$, $TiO_2$, $SiO_2$, $MnO_2$, $Co_2O_3$, NiO, BaO, CaO, MgO and the like, and a compound oxide-based catalyst in which $CuO$—$Cr_2O_3$ and $CuO$—$ZnO$ are main components is suitably used. Further, an alkaline metal compound may be contained as a component other than the above-mentioned components.

The catalyst may be a catalyst using a carrier or a catalyst not using a carrier. The carrier includes metal oxides and compound oxides thereof such as silica, alumina, titania, zirconia, magnesia, silica alumina and the like; bentonite, montmorillonite, diatomaceous earth, acid clay, activated carbon and the like, but silica and diatomaceous earth are preferable. Further, when the catalyst is molded, binders such as graphite, silica sol, alumina and the like may be added.

The shape of the catalyst includes spherical shape, cylindrical shape and the like, and the size of the catalyst is usually from 0.5 to 10mm, and preferably from 1 to 6mm.

The catalyst can be produced by a co-precipitation method, a precipitation method, a mixing method or the like. For example, a catalyst powder is prepared by heating a paste obtained by the co-precipitation method, the forementioned binder or the like is added to the powder, and a molded pellet is obtained by carrying out a tabletting molding or an extrusion molding.

Further, commercially available products corresponding thereto may be used.

The present invention is characterized in that a catalyst which is reduced in the presence of liquid phase is used. When copper oxide in the catalyst is usually reduced to obtain copper as active species, the reaction heat generated by the reduction is extremely large as 38kcal/mol—CuO, and a method of suppressing the reaction rate by diluting hydrogen gas as a raw material is adopted in order to efficiently remove the reaction heat.

However, according to inventor's study, it was considered that the temperature of a catalyst surface was drastically raised depending on the operational condition, Cu on the catalyst surface coagulated, the activity after the reduction was drastically lowered, and stable activity was not obtained.

Further, when hydrogen is diluted, it is not economical because a great amount of an inert gas such as nitrogen or the like is required.

In the present invention, since heat capacity removed in reduction in the presence of liquid phase is large as compared with that in reduction in the absence of liquid phase, the reaction heat generated in the reduction can be efficiently removed, and further, since only hydrogen which solved in liquid phase contributes the reaction, the reaction can be controlled to a desired rate by changing a pressure, temperature or the like without dilution of hydrogen, or in dilution with a minor amount of a diluting gas. Accordingly, it is extremely economical from the viewpoint of industrial performance, the lowering of activity caused by coagulation of copper is not observed, and a catalyst having a stable activity can be obtained.

As a liquid medium, any of those which is liquid under reduction condition can be used, and specific examples thereof include water, alcohols such as methanol, ethanol, propanol, ethyleneglycol mono methyl ether, α-phenylethyl alcohol and the like; ethers such as diethyl ether, tetrahydrofuran, dioxane, ethylene glycol dimethyl ether and the like; hydrocarbons such as hexane, heptane, toluene, ethyl benzene and the like; and mixed solvents thereof.

The reduction-treated copper-based catalyst of the present invention can be used for hydrogenation of organic compounds such as acetophenone and the like.

The reduction-treated copper-based catalyst of the invention can be suitably applied to hydrogenation of acetophenone for producing α-phenylethyl alcohol.

The hydrogenation of acetophenone is carried out using a reactor in which the above-mentioned catalyst is packed. The reaction temperature is usually 40 to 200° C., and preferably 60 to 150° C. The reaction pressure is usually from 0.1 to 20Mpa and preferably from 1 to 10 Mpa. When the temperature or the pressure is too low, the reaction does not sufficiently proceed, and on the other hand, when the temperature or the pressure is too high, the by-production of ethylbenzene may increase. The amount of a catalyst used is usually from 0.01 to 50 $hr^{-1}$ as the space velocity of a raw material liquid to a catalyst layer and preferably from 0.1 to 20 $hr^{-1}$. The amount of hydrogen fed is usually from 1.0 to 3-fold by mole for the amount of acetophenone in the raw material liquid charged.

As a liquid medium for reaction, those above-mentioned, which are used in the reduction-treatment of the copper-based catalyst, can be used.

In the reduction-treatment or hydrogenation mentioned above, the liquid or gas from the exit of a reactor may be recycled to the reactor.

Then, the present invention is illustrated according to Examples in detail, but is not limited thereto.

EXAMPLE 1

In a reaction tube having an inner diameter of 1 cm and a packing height of 1 m of a fixed bed adiabatic reactor, 70 cc of a copper silica pellet catalyst (containing 65% by weight of CuO) was filled, 100 g/hr of ethylbenzene (hereinafter, described as "EB") and 10000 Ncc/hr of a gas composed of 15% of methane and 85% of hydrogen were fed at a pressure of 0.6 Mpa and a temperature of 150° C., and reduction was carried out for 20 hours. After completion of the reduction, 427 g/hr of a flesh raw material liquid composed of 22% by weight of acetophenone (hereinafter, described as "ACP"), 61% by weight of α-phenylethyl alcohol (hereinafter, described as "MBA"), and 17% by weight of other compounds, and 35.6 NL/hr converted to normal state (the molar ratio of hydrogen to acetophenone raw material is 1.5-fold by mol) of a mix gas composed of 83% by volume of hydrogen and 17% by volume of methane were fed, and hydrogenation reaction was carried out at a pressure condition of 2.5 MPa. At a stationary state after 8 hours in which the inlet temperature of the reactor was controlled at 90° C., reaction results determined from compositions at the inlet and exit of the reactor were 68.3% as an ACP conversion, and 0.8% as EB selectivity.

COMPARATIVE EXAMPLE 1

In a reaction tube having an inner diameter of 1 cm and a packing height of 1 m of a fixed bed adiaba 70 cc of a copper silica pellet catalyst (containing 65% by weight of CuO) was filled, 8500 Ncc/hr of a gas composed of 15% of methane and 85% of hydrogen was fed at a pressure of 0.1 Mpa and a temperature of 140 to 180° C. while diluting it with nitrogen of 3500 Ncc/hr, and reduction was carried out for 20 hours. After completion of the reduction, 428 g/hr of a flesh raw material solution composed of 21% by weight of acetophenone (hereinafter, described as "ACP") and 79% by weight of α-phenylethyl alcohol (hereinafter, described as "MBA"), and 35.6 NL/hr converted to normal state (the molar ratio of hydrogen to acetophenone raw material is 1.5-fold by mol) of a mix gas composed of 86% by volume of hydrogen and 14% by volume of methane were fed, and hydrogenation reaction was carried out under a pressure condition of 2.5 MPa.

At a steady state after 8 hours in which the inlet temperature of the reactor was controlled at 90° C., reaction results determined from compositions at the inlet and exit of the reactor were 58.3% as an ACP conversion, and 1.4% as EB selectivity.

As described above, according to the present invention, a process for producing α-phenylethyl alcohol by hydrogenating acetophenone in the presence of a copper-based catalyst, which can keep the lowering of catalyst activity at an extremely low level can be provided.

What is claimed is:

1. A process for producing α-phenylethyl alcohol, which comprises reducing a copper-based catalyst comprising 10 to 90% by weight of CuO with hydrogen in the presence of a liquid medium to obtain a reduced copper-base catalyst, and subsequently contacting said reduced catalyst with acetophenone under hydrogenation conditions to produce α-phenylethyl alcohol.

2. The process according to claim 1, wherein the hydrogenation conditions include a temperature of 40 to 200° C.

3. The process according to claim 1, wherein the copper-based catalyst comprises from 20 to 80% by weight of CuO.

4. The process according to claim 3, wherein the hydrogenation conditions include a temperature of 40 to 200° C.

* * * * *